United States Patent [19]
Roline et al.

[11] Patent Number: 5,320,643
[45] Date of Patent: Jun. 14, 1994

[54] AUTOMATIC CARDIAC CAPTURE RESTORATION AND THRESHOLD-SEEKING METHOD AND APPARATUS

[75] Inventors: Glenn M. Roline, Anoka; Lucy M. Nichols, Maple Grove; Tommy D. Bennett, Shoreview; David L. Thompson, Fridley, all of Minn.

[73] Assignee: Medtronic, Inc., Minneapolis, Minn.

[21] Appl. No.: 958,194

[22] Filed: Oct. 6, 1992

[51] Int. Cl.$^5$ .......................... A61N 1/365
[52] U.S. Cl. ......................... 607/28; 607/11; 607/23
[58] Field of Search ............ 607/11, 28, 17, 23

[56] References Cited

U.S. PATENT DOCUMENTS

| | | | |
|---|---|---|---|
| 3,638,656 | 2/1972 | Grandjean et al. | 607/28 |
| 3,713,449 | 1/1973 | Mulier | 607/11 |
| 3,920,024 | 11/1975 | Bowers | 607/11 |
| 4,428,378 | 1/1984 | Anderson et al. | 128/419 |
| 4,485,813 | 12/1984 | Anderson et al. | 128/675 |
| 4,556,063 | 12/1985 | Thompson et al. | 128/419 |
| 4,686,988 | 8/1987 | Sholder | 607/28 |
| 4,708,142 | 11/1987 | DeCote, Jr. | 607/28 |
| 4,729,376 | 3/1988 | DeCote, Jr. | 607/28 |
| 4,895,152 | 1/1990 | Callaghan et al. | 607/28 |
| 4,979,507 | 12/1990 | Heinz et al. | 607/28 |
| 5,105,810 | 4/1992 | Collins et al. | 607/9 |
| 5,127,404 | 7/1992 | Wyborny et al. | 128/419 |
| 5,154,170 | 10/1992 | Bennett et al. | 128/419 |
| 5,222,493 | 6/1993 | Sholder | 607/28 |

Primary Examiner—William E. Kamm
Assistant Examiner—Kennedy J. Schaetzle
Attorney, Agent, or Firm—Gregory P. Gadson; Harold R. Patton

[57] ABSTRACT

An automatic capture restoration and threshold-seeking method and apparatus for use with a cardiac pacemaker derives control signals for restoring cardiac capture from a cardiac pressure sensor. The pressure sensor also provides input control signals for a threshold-seeking apparatus. Both pulse width and amplitude thresholds can be changed contemporaneously during both capture restoration and threshold seeking.

4 Claims, 6 Drawing Sheets

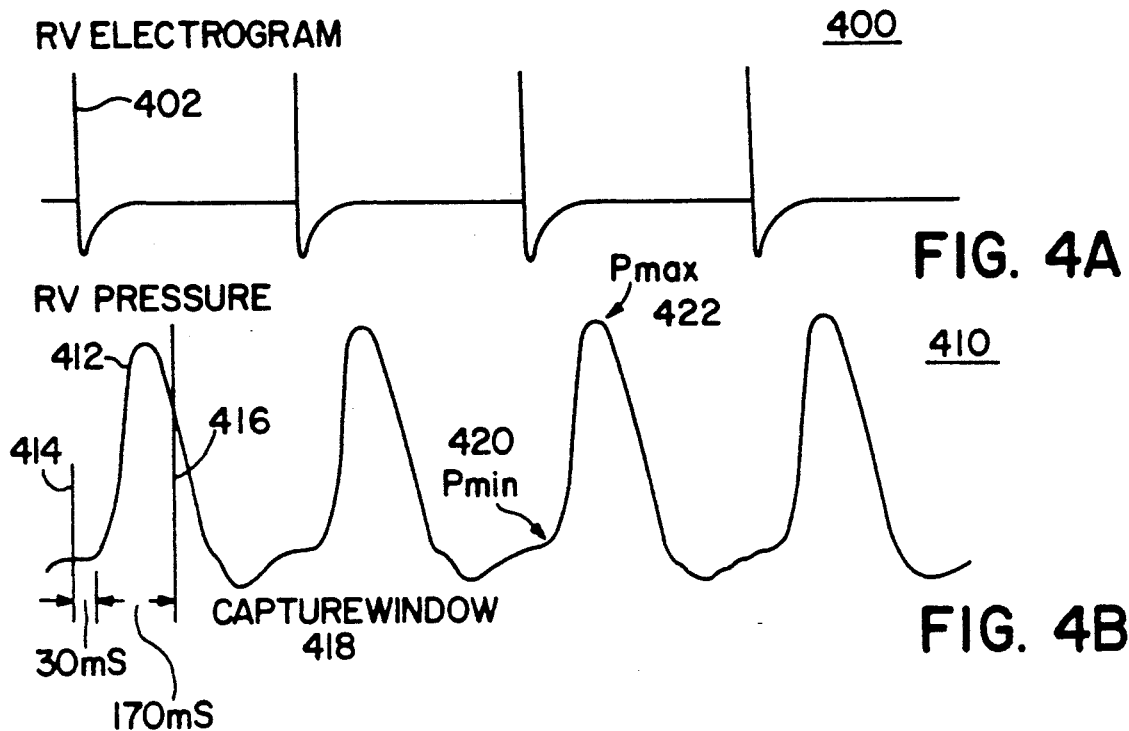
FIG. 4A
FIG. 4B
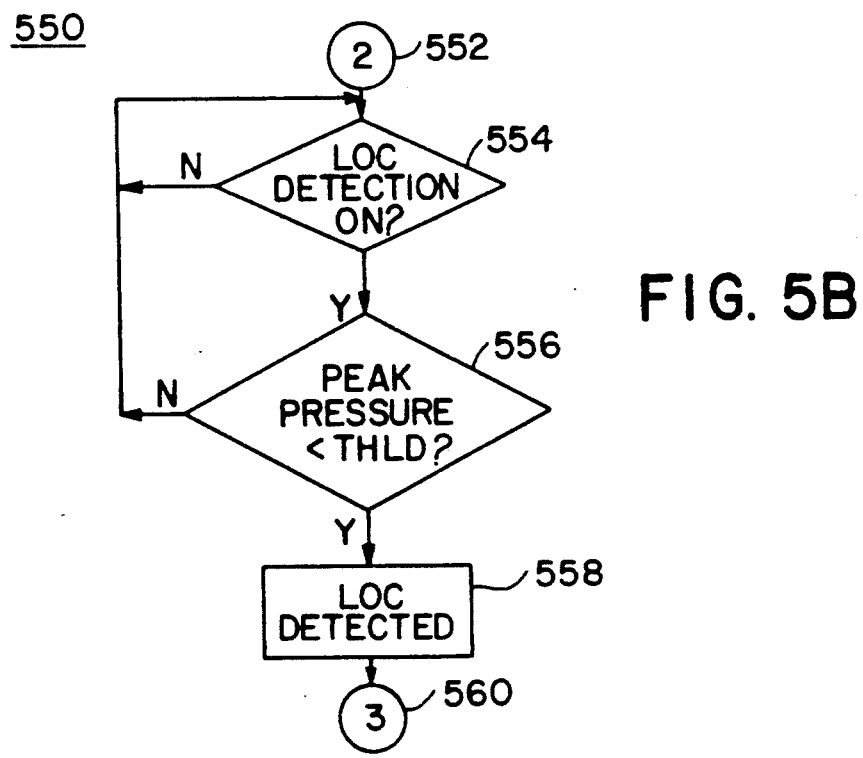
FIG. 5B

AUTOMATIC CARDIAC CAPTURE RESTORATION AND THRESHOLD-SEEKING METHOD AND APPARATUS

FIELD OF THE INVENTION

The present invention generally relates to "capture" of the heart, here defined as the presence of contractions in the heart in direct response to electrical stimulation signals emanating from an artificial pacemaker ("pacemaker"). Also, the present invention relates to adjusting stimulation signal thresholds for pacemaker energy efficiency.

BACKGROUND OF THE INVENTION

Generally speaking, a cardiac pacemaker is an electrical device used to supplant some or all of an abnormal heart's natural pacing function, by delivering appropriately timed electrical stimulation signals designed to cause the myocardium of the heart to contract or "beat". Stimulation signals usually have well-defined amplitude and pulse width characteristics which can be adjusted to meet physiologic and device power conservation needs.

The strength (amplitude) and duration (pulse width) of the stimulation signals must be of such magnitude that capture is maintained, to prevent serious complications and even death. Yet, it is desirable for these magnitudes not to be higher than is needed for a reasonable safety margin for longer battery life. Chief among the problems is that stimulation signal thresholds necessary for maintaining capture often fluctuate in the short term, and gradually change in the long term. It has been clinically observed that the lowest threshold is observed immediately after implantation of the pacemaker (the acute threshold). Inflammation in the tissue around the tip of the stimulation electrode requires greater energy to propagate the stimulation signals, thereby driving the threshold up sharply during the first two to six weeks to its highest level (the peak threshold). Some of the inflammation reduces over the long-term, to lower the threshold below the peak level—the chronic threshold. However, the chronic threshold does not reduce to the acute level, since some permanent fibrous tissue, requiring greater energy than non-fibrous tissue for signal propagation, remains around the electrode tip. In the short-term, thresholds may decrease with exercise, for example, and may increase with various activities, including sleep.

Some prior art implantable pulse generators (IPGs) which serve as cardiac pacemakers have an automatic capture feature to maintain capture without the need for clinical or patient intervention. These IPGs typically rely upon electrical sensors similar to pacing leads (consisting of insulated conducting wire, electrode tips and a connector for connecting the lead to the IPG) to sense the presence of capture in response to the stimulation signals. The function and accuracy of the these sensors have been adversely affected by one or more of factors including, but not limited to: myopotentials (electrical signals which are the product of muscle movement); stray electromagnetic interference (EMI); problems with the sensor sensitivity (either too sensitive or not sensitive enough); and variations of the sensed electrical signals as a result of changes in thoracic pressure (for example, due to respiration, coughing or sneezing).

SUMMARY OF THE INVENTION

In view of the foregoing, it is a first object of the present invention to provide a cardiac pacemaker having an automatic capture ("auto-capture") feature in which its capture/threshold sensors are unaffected by myopotentials.

It is a second object of the present invention to provide a cardiac pacemaker with auto-capture in which its capture/threshold sensors are unaffected by EMI.

It is a third object of the present invention to provide a cardiac pacemaker with auto-capture in which its capture/threshold sensors have stable sensitivities.

It is a fourth object of the present invention to provide a cardiac pacemaker with auto-capture in which its capture/threshold sensors are unaffected by changes in thoracic pressure.

In addition to the above, it is a fifth object of the present invention to provide a cardiac pacemaker with improved threshold-seeking capabilities following the restoration of capture.

In order to satisfy the above objects and others, the present invention provides a cardiac pacemaker system capable of automatically capturing a heart by adjusting cardiac stimulation signals, the system at least including:

pressure sensing means coupled to the heart for sensing pressure indicia related to capture, vel non, in at least one chamber of the heart; and capture control means coupled to the pressure sensing means for, in response to the pressure indicia corresponding to loss of capture, controlling the stimulation signals in a manner to restore capture.

The present invention further provides a cardiac pacemaker system capable of automatically seeking stimulation signal thresholds to increase power efficiency, the system at least including:

pressure sensing means coupled to the heart for sensing pressure indicia related to heart contractility in at least one chamber of the heart; and threshold control means coupled to the pressure sensing means for controlling the stimulation signals in a manner to seek efficient stimulation signal thresholds in response to the pressure indicia.

And, the present invention provides a cardiac pacemaker capable of automatically seeking stimulation signal thresholds to increase power efficiency at least including:

capture detection means for detecting capture of a heart;

amplitude seeking means coupled to the capture detection means for seeking amplitude thresholds of the stimulation signals; and pulse width seeking means coupled to the capture detection means for seeking pulse width thresholds of the stimulation signals;

wherein amplitude thresholds and pulse width thresholds may be changed contemporaneously.

The details of the present invention will be revealed in the following description, with reference to the attached drawing.

BRIEF DESCRIPTION OF THE DRAWING

The various figures of the drawing are briefly described as follows:

FIG. 4A is a graphical representation of the signals seen on the pacing lead by the sense amplifier.

FIG. 4B is a graphical representation of the signals seen by a right ventricular indwelling pressure sensor.

FIG. 5B is a flow chart illustrating the present invention's pressure measuring program/routine.

DETAILED DESCRIPTION OF THE INVENTION

Part I. Description of Pacemaker Device

Figure 1:
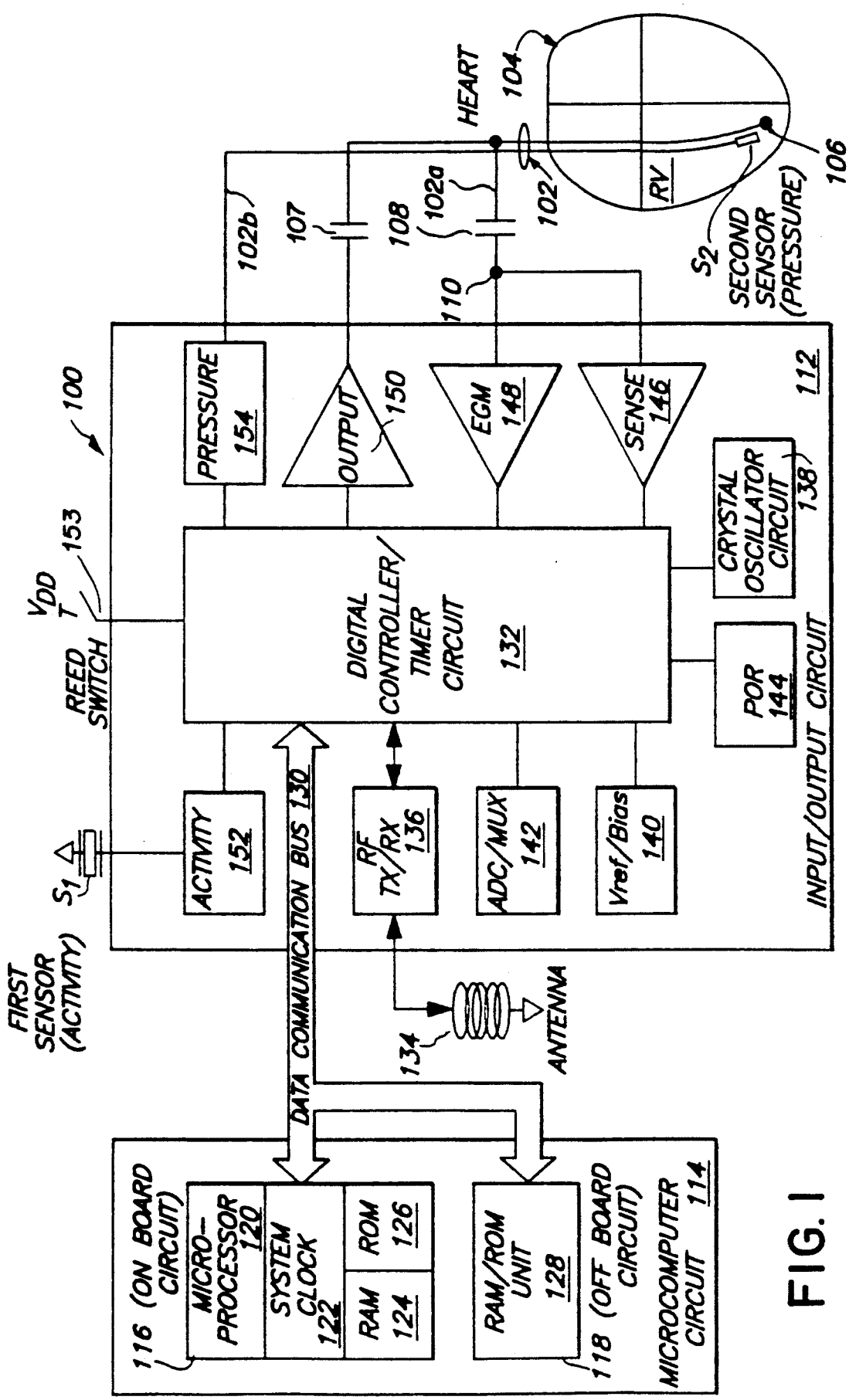
FIG. 1 is a schematic block diagram of a multi-sensor, rate-responsive, single chamber IPG capable of subsuming the present invention.

FIG. 1 is a block circuit diagram illustrating a multi-programmable, implantable, single-chamber, bradycardia pacemaker 100 capable of carrying out the present invention. This figure and related figures not presented in this letters patent are described in U.S. patent application Ser. No. 07/567,476, filed Aug. 14, 1990, and titled OPTIMIZATION FOR RATE RESPONSIVE CARDIAC PACEMAKER, which application is hereby incorporated by reference. Although the present invention is described in conjunction with a microprocessor-based architecture, it will be understood that it could be implemented in other technology such as digital logic-based, custom integrated circuit (IC) architecture, if desired. It will also be understood that the present invention may be implemented in dual-chamber pacemakers, cardioverters, defibrillators and the like.

In the preferred embodiment of FIG. 1, pacemaker 100 includes two sensors, namely, $S_1$ and $S_2$, each of which provide a sensor output which varies as a function of a measured parameter that relates to the metabolic requirements of the patient. Since each sensor output can be utilized by pacemaker 100 to control its pacing rate, each sensor output is herein referred to as a rate-control parameter (RCP). Examples of an RCP include, for example, physical activity of the body, right ventricular blood pressure and the change of right ventricular blood pressure over time, venous blood temperature, venous blood oxygen saturation, respiration rate, minute ventilation, and various pre- and post-systolic time intervals measured by impedance or pressure sensing within the right ventricle of the heart.

In the preferred embodiment, first sensor $S_1$ comprises an activity sensor, such as a piezoelectric sensor of the type disclosed in U.S. Pat. No. 4,428,378 issued to Anderson et al., entitled "Rate Adaptive Pacer", which is held by the same assignee as the present invention and which is incorporated herein by reference. First sensor $S_1$ thus measures a rate-control parameter related to physiologic forces associated with body activity ($RCP_{act}$), and provides a first sensor output ($Output_{act}$) which is proportional to the patient's activity. Also in the preferred embodiment, second sensor $S_2$ comprises a dynamic pressure sensor, such as the type disclosed in U.S. Pat. No. 4,485,813 issued to Anderson et al., entitled "Implantable Dynamic Pressure Transducer System", which is held by the same assignee as the present invention and which is incorporated by herein by reference. Second sensor $S_2$ thus measures a rate-control parameter related to changes in fluid pressure in the heart associated with its mechanical activity and contractility ($RCP_{press}$), and provides a second sensor output ($Output_{press}$) which is proportional to the magnitude of the change in fluid pressure in the patient's heart. In the preferred embodiment, second sensor output $S_2$ is processed to derive a peak positive time derivative of the fluid pressure applied to the pressure sensor $S_2$ within the right ventricle of the patient's heart (i.e., $dP/dt_{max}$).

Pacemaker 100 is schematically shown electrically coupled via a pacing lead 102 to a patient's heart 104. Lead 102 includes an intracardiac electrode 106 and second sensor $S_2$ which are located near the distal end of lead 102 and positioned within the right ventricle (RV) of the patient's heart. Lead 102 can carry either unipolar or bipolar electrodes as is well known in the art. In the preferred embodiment, the lead 102 which couples pacemaker 100 to the ventricular endocardium can comprise a steroid-tipped, unipolar lead with an integral pressure transducer of the type described above. Electrode 106 is coupled via suitable lead conductor 102a through input filter capacitor 108 to node 110 and to the input terminals of an Input/Output Circuit shown at block 112. Output from first sensor $S_1$ is coupled to Input/Output Circuit 112. Output from second sensor $S_2$ is also coupled to Input/Output Circuit 112 via suitable lead conductor 102b.

Input/Output Circuit 112 contains the operating input and output analog circuits for digital controlling and timing circuits necessary for the detection of electrical signals derived from the heart, such as the cardiac electrogram, output from the first sensor output $S_1$, and output from the second sensor output $S_2$, as well as for the application of stimulating pulses to the heart to control its rate as a function thereof under the control of software-implemented algorithms in a Microcomputer Circuit shown at 114.

Microcomputer Circuit 114 comprises an On-Board Circuit 116 and an Off-Board Circuit 118. On-Board Circuit 116 includes a microprocessor 120, a system clock 122, and on-board RAM 124 and ROM 126. Off-Board Circuit 118 includes an off-board RAM/ROM Unit 128. Microcomputer Circuit 114 is coupled by Data Communication Bus 130 to a Digital Controller/Timer Circuit shown at 132. Microcomputer Circuit 114 may be fabricated of custom IC devices augmented by standard RAM/ROM components.

It will be understood by those skilled in the art that the electrical components represented in FIG. 1 are powered by an appropriate implantable-grade battery power source (not shown).

An antenna 134 is connected to Input/Output Circuit 112 for purposes of uplink/downlink telemetry through a radio frequency (RF) Transmitter/Receiver Circuit (RF TX/RX) shown at 136. Telemetering both analog and digital data between antenna 134 and an external device, such as an external programmer (not shown), is accomplished in the preferred embodiment by means of all data first being digitally encoded and then pulse position modulated on a damped RF carrier, as substantially described in U.S. Pat. No. 5,127,404, issued on Jul. 7, 1992, entitled "Telemetry Format for Implantable Medical Device", which is held by the same assignee as the present invention and which is incorporated herein by reference. A reed switch 153 is connected to Input/Output Circuit 112 to enable patient follow-up via disabling the sense amplifier 146 and enabling telemetry and programming functions, as is known in the art.

A Crystal Oscillator Circuit 138, typically a 32,768 Hz crystal-controlled oscillator, provides main timing clock signals to Digital Controller/Timer Circuit 132. A Vref/Bias Circuit 140 generates a stable voltage reference and bias currents for the analog circuits of Input/Output Circuit 112. An ADC/Multiplexer Circuit (ADC/MUX) 142 digitizes analog signals and voltages to provide telemetry and replacement time-indicating or end-of-life function (EOL). A Power-on-Reset Circuit (POR) 144 functions to initialize the pacemaker 100 with programmed values during power-up, and reset the program values to default states upon the detection of a low battery condition or transiently in the presence of certain undesirable conditions such as unacceptably high EMI, for example.

The operating commands for controlling the timing of the pacemaker depicted in FIG. 1 are coupled by bus 130 to Digital Controller/Timer Circuit 132 wherein digital timers set the overall escape interval of the pacemaker, as well as various refractory, blanking and other timing windows for controlling the operation of the peripheral components within Input/Output Circuit 132.

Digital Controller/Timer Circuit 132 is coupled to a sense amplifier (SENSE) 146 and an electrogram (EGM) amplifier 148 for receiving amplified and processed signals picked up from electrode 106 through lead conductor 102a and capacitor 108 representative of the electrical activity of the patient's heart 104. SENSE amplifier 146 produces a sense event signal for re-setting the escape interval timer within Circuit 132. The electrogram signal developed by EGM amplifier 148 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", which is held by the same assignee as the present invention and which is incorporated by herein by reference. An output pulse generator 150 provides the pacing stimulus to the patient's heart 104 through an output capacitor 107 and lead 102 in response to a paced trigger signal developed by Digital Controller/Timer Circuit 132 each time the escape interval times out, or an externally transmitted pacing command has been received, or in response to other stored commands as is well known in the pacing art.

Digital Controller/Timer Circuit 132 is coupled to a processing/amplifying circuit (ACTIVITY) 152 for receiving amplified and processed sensor output (Output$_{act}$) from first sensor S$_1$ and associated ACTIVITY circuitry which is representative of activity. Digital Controller/Timer Circuit 132 is coupled to a processing/amplifying circuit (PRESSURE) 154 for receiving amplified and processed sensor output (Output$_{press}$) from second sensor S$_2$ through lead Conductor 102b representative of changes in fluid pressure in the patient's heart 104, for use in rate response control, and others functions as desired.

In a preferred embodiment of the present invention, pacemaker 100 is capable of operating in various non-rate-responsive modes which include VVI, VOO and VVT, as well as corresponding rate-responsive modes of VVIR, VOOR and VVTR. Further, pacemaker 100 can be programmably configured to operate such that it varies its rate only in response to one selected sensor output, or in response to both sensor outputs, if desired (i.e., utilizing either or both of Output$_{act}$ or Output$_{press}$).

Part II. Definitions

For purposes of describing this invention, a definition of additional relevant terms follows:

Detection Window - A 170 mSec window beginning 30 mSec after a paced or sensed event used to detect the presence of a pressure signal indicative of cardiac contraction.

Loss-of-Capture (LOC) - Processing by pacemaker 100 detects the absence of a pressure signal in the detection window after a paced event. This lack of stimulated cardiac contraction is labeled Loss-of-Capture.

Lower Rate (LR) - A value supplied by the clinician which establishes a lower boundary on the pacing rate. If the sensors are disabled, or their sensor outputs are not large enough to increase rate, the lower rate is the stimulus rate. With rate response, the allowed programmable values for LR range from 40 pulses per minute (ppm) to 100 ppm at 1 ppm intervals.

Metric - The programmed (selected) output stimulus parameter (pulse width or pulse amplitude) selected to be modified in the response to Loss-of-Capture and during the Recovery sequence.

Non-Metric - The non-selected output stimulus parameter (pulse width or pulse amplitude). The non-metric parameter is changed only at the maximum output stimulus during response to Loss-of-Capture.

$P_{max}$ - Processing by pacemaker 100 determines the maximum signal level in the pressure waveform from pressure circuit 154 during a detection window.

$P_{min}$ - Processing by pacemaker 100 determines the minimum signal level in the pressure waveform from pressure circuit 154 during a detection window.

Pulse Pressure Average (PRESS.AVG) - Dynamic pressure sensor S$_2$ is disposed in the right ventricle (RV) of the patient's heart to sense fluid pressure therein (RCP$_{press}$), and to provide a sensor output (Output$_{press}$) related to changes in the fluid pressure associated with the heart's mechanical activity and contractility. Processing by pacemaker 100 of Output$_{press}$ yields a peak pulse pressure (PRESS.PK) which is proportional to the magnitude of such RV pressure changes. Each sensed or paced RV event will yield a peak pulse pressure signal. In the preferred embodiment, a running average of the last 16 valid PRESS.PK values are used to determine an average peak pulse pressure value, referred to as the "PRESS.AVG". Pacemaker 100 tests for validity of each peak pulse pressure value on a sample-by-sample basis, based upon the requirement that the sampled PRESS.PK value must be equal to or greater than, 4 mm Hg. Values below this validity threshold are ignored. Once determined, PRESS.AVG is used to detect capture on a cycle-to-cycle basis.

Recovery - Pacemaker 100 automatically attempts to adjust output stimulus parameters 1 hour after a Loss-of-Capture sequence. The metric parameter is adjusted in small increments toward it's programmed value.

Response to LOC - Pacemaker 100 automatically responds to a LOC by increasing the output pulse width and/or amplitude in a controlled response to enable rapid restoration of cardiac stimulation.

Threshold - A programmable threshold of continuously averaged peak pulse pressure value based upon a percentage of this stored peak value. The programmable range is 25-75% in 12.5% steps.

Upper Rate (UR) - A value supplied by the clinician which limits the maximum stimulation rate when the rate responsive modes for activity, pressure, or both combined, are in effect, or when response to loss-of-capture pacing is occurring such that the pacing rate generated by pacemaker 100 does not become hemodynamically excessive. The allowed programmable values range from 100 ppm to 175 ppm at 5 ppm intervals, provided UR must also be at least 20 ppm greater than Lower Rate (LR) and Resting Rate (REST.RATE).

Part III. Sensors

A brief description of measurement of the rate control parameter for activity ($RCP_{act}$) now follows. The activity sensor $S_1$ sensor employed is a piezoelectric crystal transducer of the type described in the above-mentioned '378 Anderson et al. patent, which is mounted to the interior surface of the pacemaker can as disclosed therein. Sensor $S_1$ generates a sensor output ($Output_{act}$) due to deflection of the pacemaker can as a result of compression waves within the body caused by physical movement of the body. Processing by ACTIVITY circuit 152 is performed, such that each event in which the amplitude of $Output_{act}$ exceeds a programmed Activity Threshold (ACT.THRESH) is then counted and retained in an Activity Count (ACT.COUNT) of pacemaker 100. ACT.COUNT is used to calculate the activity-based Target Rate ($STR_{act}$) on a cycle-to-cycle basis.

A brief description of measurement of the rate control parameter for pressure ($RCP_{press}$) now follows. The pressure sensor $S_2$ sensor employed is a dynamic pressure sensor of the type described in the above-mentioned '813 Anderson et al. patent. Sensor $S_2$ is disposed in the right ventricle (RV) of the patient's heart to sense fluid pressure therein ($RCP_{press}$), and to provide a sensor output ($Output_{press}$) related to changes in the fluid pressure associated with the heart's mechanical activity and contractility. Processing by PRESSURE circuit 154 of $Output_{press}$ yields a peak positive first time derivative thereof ($dP/dt_{max}$) which is proportional to the magnitude of such RV pressure changes. Each sensed or paced RV event will yield a peak positive $dP/dt_{max}$ signal, although a peak negative signal may be used as an alternative. In the preferred embodiment, the last 8 valid $dP/dt_{max}$ values are used to determine an average $dp/dt_{max}$ value, referred to as the "Pressure (dP/dt) Average" or "dP/dt.AVG". Pacemaker 100 tests for validity of each $dP/dt_{max}$ value on a sample-by-sample basis, based upon the requirement that a sampled $dP/dt_{max}$ value must be within a predetermined range defined by a $dP/dt_{max}$ value associated with the patient's Resting Rate (REST.PRESS). In the preferred embodiment, this validity range is defined as $dP/dt_{max}$ values between 25% to 400% of REST.PRESS. Values outside this validity range are ignored. Once determined, PRESS.AVG is used to calculate the pressure-based Sensor Target Rate ($STR_{press}$) on a cycle-to-cycle basis.

It will be understood, however, that the present invention can be practiced with more than two sensors, or with sensors of a type other than the ones above described. In the preferred embodiment, however, various advantages are obtained by the use of the particular sensors in the specific combination stated above.

For example, an activity-based sensor provides a fast and repeatable response to physical activity. Sensors of this type have been exhaustively reported in clinical literature, and their safety and efficacy are well-documented. Additionally, such sensors offer the advantage of being less affected by changes in a patient's health or disease status, and thus provide more predictable behavior over time. However, there are also theoretical and practical limitations to the behavior of activity sensors. For example, they respond only to physical activity. Therefore, patients undergoing other types of physiological stresses which would normally evoke a heart rate response, such as thermal stress associated with normal exposure to wide variations in ambient temperature, or postural stress associated with changing from lying down to an erect position, will tend to obtain only very limited rate adjustment and their adjustment to such stresses will thus be less than entirely adequate. Additionally, the time course of rate recovery after an activity event tends to be limited by the design constraints of the pacemaker system which are not generally capable of providing a highly physiologically-based recovery function.

Consequently, the preferred embodiment also incorporates a dynamic pressure sensor for continuous measurement of cardiac pressures on a beat-by-beat basis. This sensor provides for more physiological responses than activity alone, and helps to complement the rate response provided by the activity sensor. The sensed physiologic variable in this system comprises the rate of increase in pressure within the right ventricle of the heart (i.e., a peak positive dP/dt). This variable is related to the vigor of contraction of the cardiac muscle, which in turn is regulated by the autonomic nervous system. Thus, any stress which elicits a response by the autonomic nervous system in the patient (and would cause a heart rate response in a normal individual), will also yield a heart rate response in the patient by means of the pacemaker system of the present invention. Additionally, the time course of recovery of the cardiac pressure following stresses follows the physiologic time course determined by the status of the autonomic nervous system, such that the present device will provide for pacing rate recovery which is more physiological than that which can be provided by activity sensors alone.

It can thus be appreciated that the particular sensor combination described above yields significantly improved rate response function for pacemaker 100.

Part IV. Auto-Capture and Threshold-Seeking Features

Details of the capture restoration feature of the present invention follow below.

Figure 2:
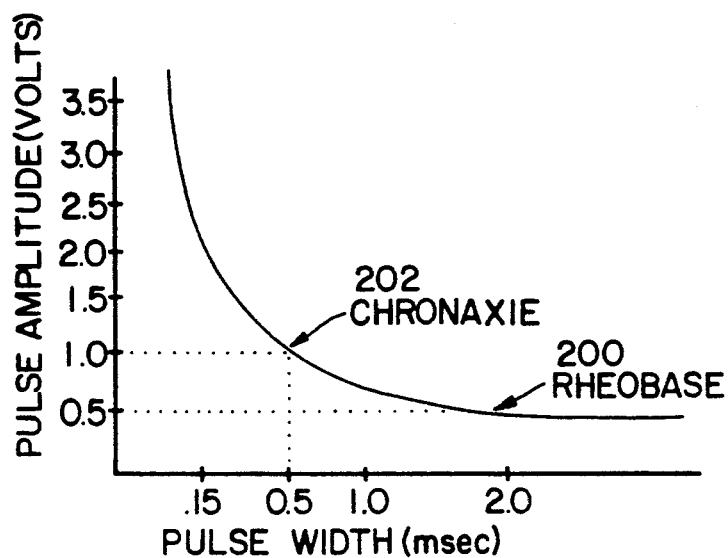
FIG. 2 is a typical strength-duration curve for cardiac stimulation signals.

FIG. 2 shows a typical strength-duration curve for electrical stimulation of myocardial tissue plotted as pulse amplitude in volts versus pulse width in milliseconds. The graph shows, inter alia, that the threshold increases with a decreasing pulse width, and thus decreases with an increasing pulse width, except that beyond the rheobase 200, no further reductions in the threshold can be achieved. Thus, increasing the pulse width beyond 2 milliseconds in the example shown still requires a threshold of 0.5 volts. Also included on the graph for illustrative purposes is the chronaxie 202, a measure of myocardial excitability, which is the point representing the lowest pulse width needed to have twice the rheobasic threshold. It is well known in the art to provide a safety margin between the actual amplitudes of stimulation signals and the thresholds from the strength-duration curve. However, as previously stated, the amount of safety margin may change over time and must be balanced against the need to maximize battery life, as increased amplitude and pulse width will cause a greater battery energy consumption.

Physiological changes in the patient may alter the thresholds from the initial programmed value or values, and can lead to loss of capture, with inadequate amplitude or pulse width. The pacemaker 100 is capable of detecting loss of capture via the pressure sensor $S_2$, described supra with reference to FIG. 1, in the form of low pulse pressure values.

The pacemaker 100 may be programmed to automatically adjust the output stimulus amplitude or pulse width to maintain capture. This programmed parameter (amplitude or pulse width) is labeled herein the programmed pulse metric. This metric parameter is adjusted throughout the response to Loss-of-Capture and recovery procedure described herein below. The other parameter (pulse width or amplitude) is labeled the non-metric and remains at it's programmed value until the third pulse in a response to Loss-of-Capture sequence as described herein below.

Figure 3:
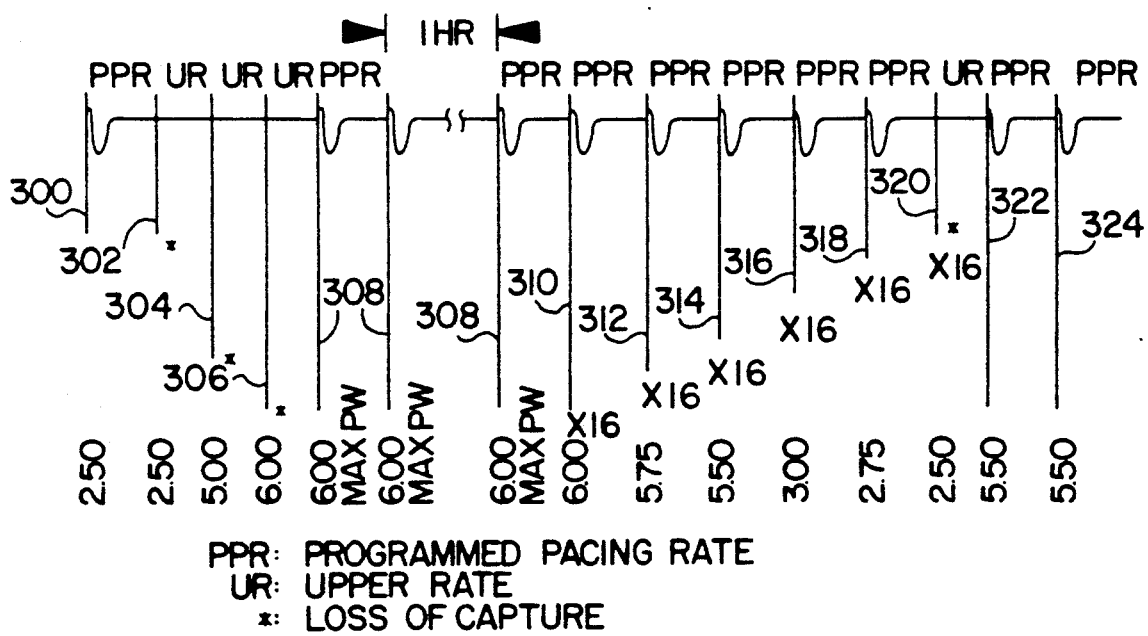
FIG. 3 is a graphical representation of the automatic capture/threshold tracking feature of the present invention.

FIG. 3 shows an electrocardiogram (ECG) which illustrates an example of a loss-of-capture condition and the response (capture restoration) of the pacemaker 100 using the pulse amplitude as the selected metric. Viewing from left to right, the first frame 300 illustrates the presence of capture by showing a ventricular beat with the pulse amplitude at 2.5 volts out of a possible 6 volts (the maximum possible pulse amplitude programmable in this preferred embodiment). At the next frame 302, however, 2.5 volts has become inadequate to maintain capture. The pacemaker immediately begins pacing at the upper rate (UR) as the first step in the capture restoration routine or program. The pulse amplitude is increased to 5 volts (based on a predefined safety margin) and 6 volts for the third (304) and fourth (306) frames, respectively (still pacing at the upper rate), but capture has still not been restored. The pulse width is then increased to its maximum value (2.0 mSec, in this embodiment), and capture is finally restored at the fifth frame 308. The pacemaker switches back to the programmed pacing rate (PPR) during that frame, and successive frames are paced at the programmed pacing rate with maximum pulse width and maximum amplitude for one hour in the preferred embodiment.

In the preferred embodiment, the second and third output pulses in the response to Loss-of-Capture are at maximum values. Alternatively, the physician may program a sequence of recovery pulse amplitudes and pulse widths less than the maximum to conserve energy in the implanted device.

The pacemaker then follows a loss-of-capture recovery routine over groups of sixteen frames (310–322) to find a smaller, but safe pulse amplitude. The first group 310 (following the one hour timeout period) restores the pulse width to its programmed value and continues pacing at 6.0 volts for 16 frames (provided capture is not lost). In the event capture is lost during any one of the 16 frames, the width is restored and the one hour timeout restarted. Capture is monitored for each of these "recovery" frames as the pulse amplitude is decremented in 0.25 volt steps at each group or 16 frame interval (312–320). In the present example, loss-of-capture again occurs at the 2.5 volt pulse amplitude level (320), causing the pacemaker to pace (322) at the upper rate and with a safety margin-increased pulse amplitude (5.5 volts since capture was last determined at 2.75 volts). Since capture is then detected at 322, the following frame 324 drops the pacing rate back to the programmed pacing rate. The pacemaker then paces at the programmed pulse width, the predetermined, safety margin-increased pulse amplitude and programmed rate for a one hour timeout period, followed again by a recovery routine. The above steps are repeated each time loss of capture is detected.

Turning now to FIG. 4A, an electrogram 400 is shown as seen on the pacing electrode 102a via the electrode 106 implanted in the right ventricle of the heart 104. FIG. 4B shows the right ventricular pressure waveform as seen by pressure circuit 154 and pressure sensor S2. The pacemaker 100 measures the pulse pressure amplitude in a window 418 beginning 30 mSec after a paced or sensed event 414, and ending 170 mSec later at 416. Peak pulse pressure is defined as $P_{max}$ (local maximum) 422 minus $P_{min}$ (local minimum) 420 in the 170 mSec window 418. While this embodiment uses a 170 mSec window for conserving energy in operating the sensor, other window intervals could be used, including continuous ones.

Figure 5A:
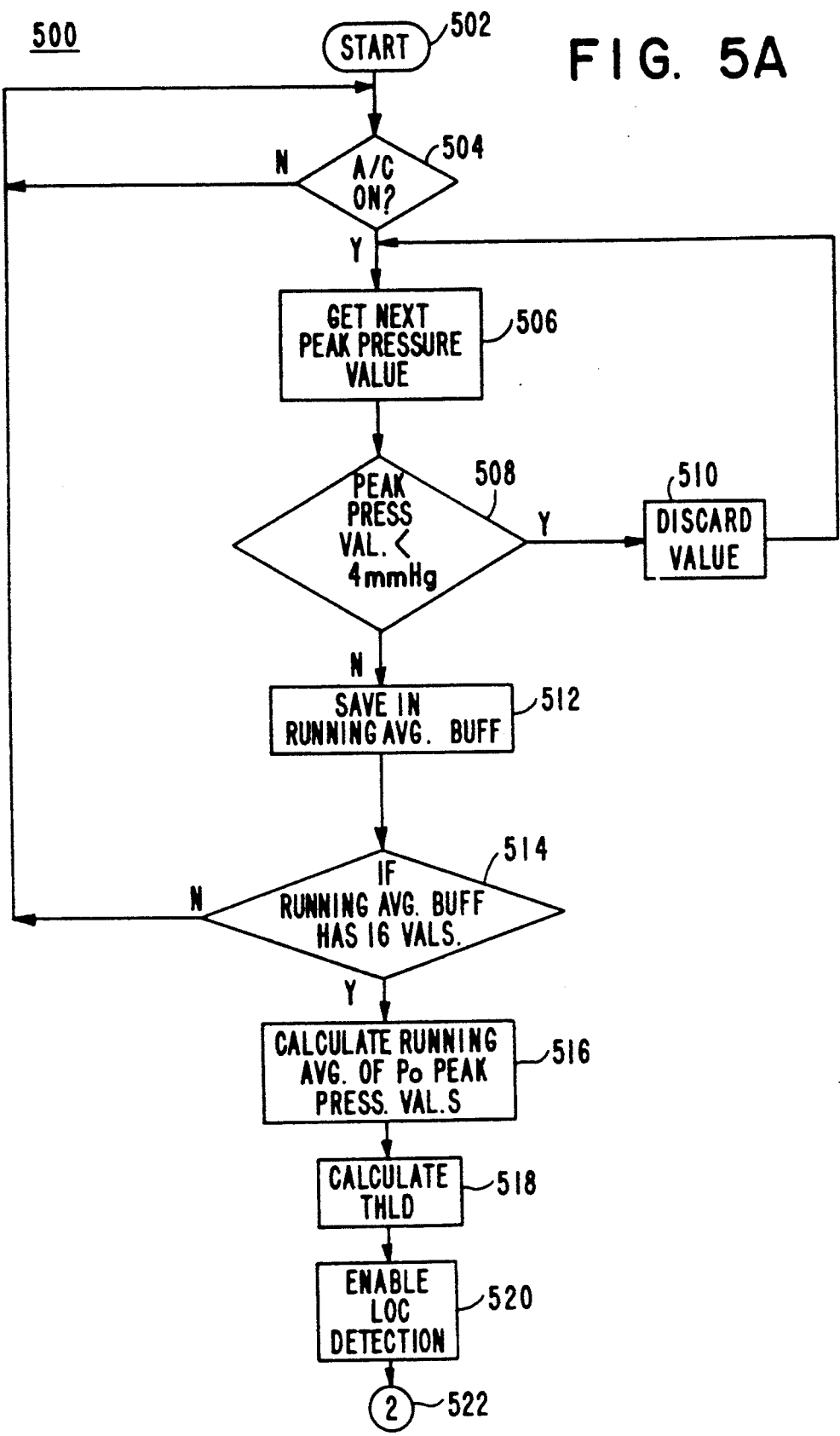
FIG. 5A is a flow chart illustrating the present invention's initialization of the pressure measuring program/routine.

FIG. 5A is a flow chart illustrating the steps used to initialize the measurement of peak pulse pressure from the sensor $S_2$ of FIG. 1. The measurement routine 500, as well as all other algorithms are controlled by the microprocessor 120 of the pacemaker 100. The pacemaker 100 starts the measurement routine 500 at 502, and at step 504, determines whether the Auto Capture algorithm is activated. If so, at step 506 the peak pulse pressure (PEAK-PRESS) signal is measured by subtracting the $P_{min}$ value from the $P_{max}$ value as measured in the 170 mSec window 418 after a paced or sensed event. Each peak pressure value is then evaluated at 508 to determine whether the peak pressure is less than 4 millimeters of Mercury (mm Hg). A value less than 4 mm Hg is discarded at step 510. A peak value equal to or greater than 4 mm Hg is saved in a buffer (RUNNING AVG.BUFF) at step 512. The pacemaker 100 then determines at step 514 whether the total count of the valid pressure peaks in RUNNING_AVG.BUFF is equal to 16. If it is not, then the measurement routine 500 returns to block 504, and repeats the routine until the count is equal to 16.

The pacemaker 100 then calculates the running average peak pressure over the previous sixteen peak pressure values at step 516, and the pressure threshold is calculated at step 518, as follows:

Threshold = Average Peak Pressure
Value × Programmed Threshold where the value of the Programmed Threshold may vary between 25 and 75 percent, and is typically 37½ percent. Once a value for pressure threshold is available, the pacemaker 100 enables the loss-of-capture detection at step 520, and exits this routine at step 522. The peak pressure running average and threshold calculations continue to be updated at 2 second intervals.

Turning now to FIG. 5B, after the LOC Detection circuit is activated at step 520 and tested at step 554, the pacemaker 100 compares, at step 556, the peak pressure value on a beat-by-beat basis to the threshold determined in step 518. If a peak pressure value is less than the threshold, capture is determined not to have occurred for that event, the routine moves to step 558, setting the LOC Detected to "TRUE", exits this diagram at 560, and enters the program 600 of FIG. 6. If on the other hand, the peak pressure value is equal to or greater than the threshold at step 518, the routine returns to step 554.

Figure 6:
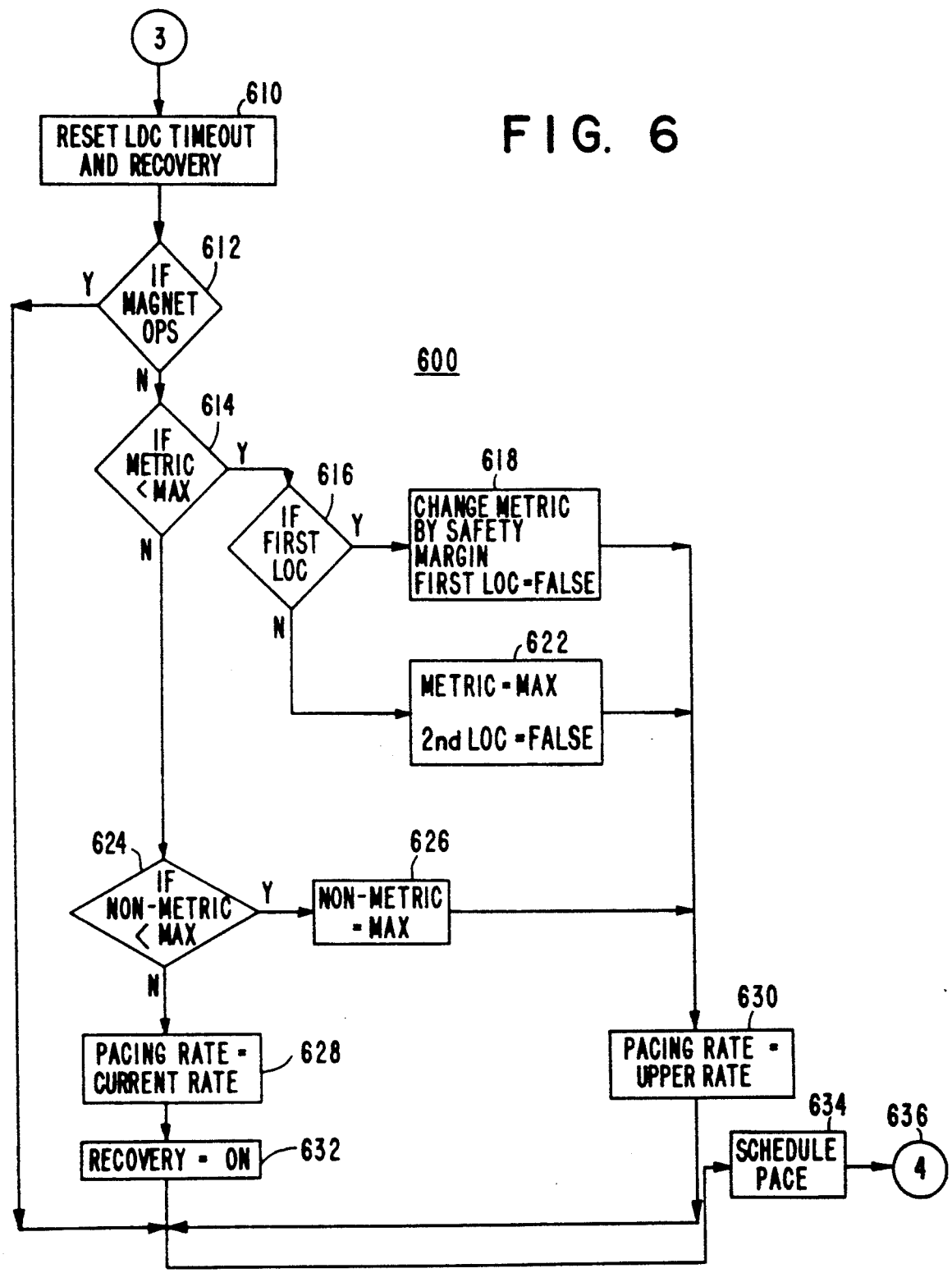
FIG. 6 is a flow chart illustrating the present invention's capture restoration program/routine for response to loss of capture.

FIG. 6 details the steps in the response to the loss-of-capture program or routine 600. Beginning with step 610, the routine resets a predefined loss-of-capture timeout counter (not shown) to "zero", and a RECOVERY flag to "off". The timeout counter increments up to a value equating to the one-hour timeout period. The RECOVERY flag signifies whether the recovery subroutine 700 (in FIG. 7) is to run (RECOVERY="on") or is not to run (RECOVERY="off"). The recovery subroutine 700 is inoperable during the operation of the restoration routine 600 and during the timeout period.

At step 612 the program determines whether the reed switch 153 is closed, signalling that the pacemaker 100 is currently receiving and/or transmitting telemetered signals. If the switch is closed, the pacemaker no longer continues the auto capture algorithm and exits the program 600 at step 636. If the reed switch is open, the program advances to step 614, where a chosen stimulation signal metric (i.e., pulse width or amplitude) is compared to its maximum value. If the maximum value of the metric has been reached, the program jumps to step 624; otherwise, the program advances to step 616.

If the metric is below the maximum value (from step 614) and the first loss of capture is being experienced (determined by checking a FIRST LOSS-OF-CAPTURE flag in step 616 for a "true" condition), then the metric is incremented by a predefined safety margin at step 618. Also, the FIRST LOSS-OF-CAPTURE flag is set to "false". The pacing rate is set at the upper rate at step 630 and a paced event is scheduled at 634. Another pass through the program 600 up to step 616 advances the program to step 622 (since the FIRST LOSS-OF-CAPTURE flag is set to "false") where the metric is increased to its maximum value. The pacing rate remains at the upper rate (step 630), and a paced event is scheduled at step 634.

Another pass through the program 600 up to 614 advances the program to step 624, where the program determines if the maximum value for the non-metric has been reached. For example, if the metric is chosen to be pulse amplitude, then the non-metric is the pulse width. If the metric (step 614) and non-metric maximums have been achieved, the current pacing rate is maintained at step 628 for the duration of the timeout period. If not, the non-metric is increased to its maximum value at step 626, the pacing rate of the pacemaker is set equal to the upper rate via step 630 and a paced event is scheduled at 634. Following step 628, the RECOVERY flag is set to "on", indicating that the subroutine 700 can now begin.

Figure 7:
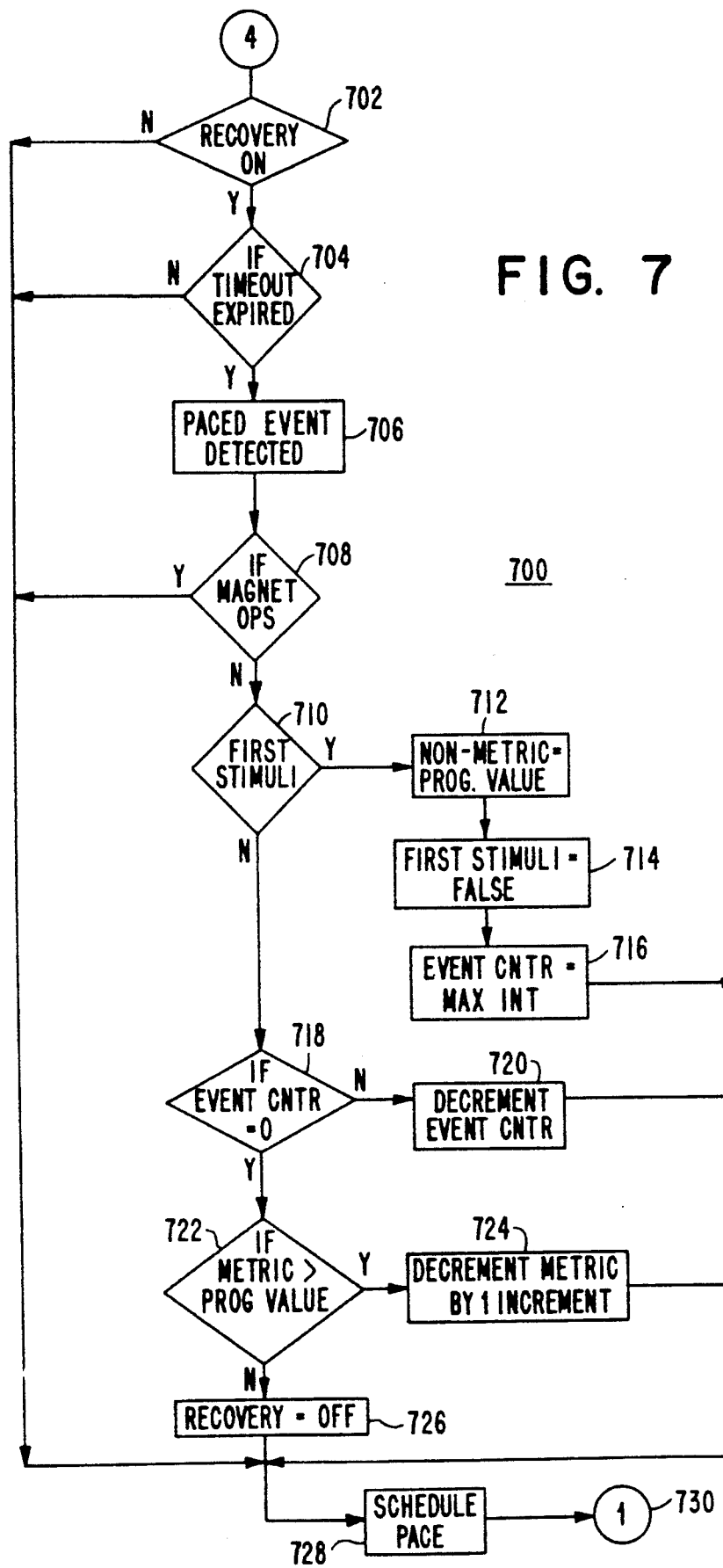
FIG. 7 is a flow chart illustrating the present invention's subroutine for recovery after capture restoration.

FIG. 7 details the recovery from loss-of-capture subroutine 700, which attempts to lower the selected metric over 16 frame sets in the preferred embodiment, to the value programmed (by the physician, for example) for chronic use. Recall that this subroutine is initiated when the recovery flag is set to the "on" state in step 632. Subroutine 700 is the threshold-seeking portion of the present invention. If the recovery subroutine has been initialized, the program 700 advances from step 702 to step 704. The recovery subroutine does not continue until the timeout counter has reached the value corresponding to the end of the timeout period. That is, when the timeout period has expired, the program advances to step 706; otherwise the program returns to its beginning step 702 after first pacing at step 728.

When a paced event is detected at step 706, the program is advanced to step 708, where the program determines whether the reed switch is closed, signalling that the pacemaker 100 is currently in a magnet mode. If the reed switch 153 is closed, the pacemaker no longer continues the recovery subroutine and returns to the beginning step 702 after pacing at step 728. If the reed switch is open, the program advances to step 710. At that step a determination is made as to whether the stimulation signal delivered is the first one, by checking a FIRST STIMULI flag for a "true" or "false" state. If so, the subroutine moves to step 712, where the non-metric is set equal to its programmed value. Afterwards, the FIRST STIMULI flag is set to the "false" state at step 714, and then an event counter (not shown) is set equal to its maximum value (16) at step 716. After the completion of step 716 the subroutine returns to step 702 for another subroutine iteration, after first pacing at step 728.

If at step 710 the first stimuli flag is "false", the subroutine jumps to step 718, where a check is made of the event counter. If the event counter reads "0", the subroutine advances to step 722; otherwise the subroutine advances to step 720, where the event counter is decremented by "1". After step 720 the subroutine is returned to the beginning step 702 after pacing at step 728. If the event counter equals "0", step 722 is then executed to determine whether the metric exceeds its programmed value. If so, the metric is decremented by 0.25 volts (pulse amplitude) or 30 μSec (pulse width) to its next lowest discrete level at step 724, and the subroutine is returned to the beginning step 702 after pacing at step 728. If the metric does not exceed its programmed value (step 722) the RECOVERY flag and hence the recovery subroutine are switched to "off" (step 726), in which state they remain until the response to loss-of-capture program 600 reactivates the subroutine. After the completion of the subroutine (step 730), the pacemaker 100 returns to the beginning of the measurement routine 500, explained supra, with respect to FIG. 5, to restart the pressure measurement, capture restoration and threshold-seeking routines, as needed.

Variations and modifications to the present invention are possible given the above disclosure. However, such variations and modifications are intended to be within the scope of the invention claimed by this letters patent.

We claim:

1. A cardiac pacemaker capable of automatically seeking stimulation signal thresholds to increase power efficiency comprising:

capture detection means for detecting capture of a heart;

amplitude seeking means coupled to said capture detection means for seeking amplitude thresholds of said stimulation signals; and pulse width seeking means coupled to said capture detection means for seeking pulse width thresholds of said stimulation signals;

wherein said pulse width seeking means comprises means for, in response to a loss-of-capture condition detected by said capture detection means, increasing said pulse width to a maximum programmed level for a predetermined timeout period, and for seeking lower pulse width thresholds when capture is maintained after the expiration of said predetermined timeout period.

2. The cardiac pacemaker in claim 1 wherein said amplitude seeking means comprises means for increasing said amplitude to a maximum programmed level during said predetermined timeout period, when capture has not been regained by said pulse width seeking means increasing said pulse width to the maximum programmed level.

3. A cardiac pacemaker capable of automatically seeking stimulation signal thresholds to increase power efficiency comprising:

capture detection means for detecting capture of a heart;
   amplitude seeking means coupled to said capture detection means for seeking amplitude thresholds of said stimulation signals; and
   pulse width seeking means coupled to said capture detection means for seeking pulse width thresholds of said stimulation signals;
   wherein said amplitude seeking means comprises means for, in response to a loss-of-capture condition detected by said capture detection means, increasing said amplitude to a maximum programmed level for a predetermined timeout period, and for seeking lower amplitude thresholds when capture is maintained after the expiration of said predetermined timeout period.

4. The cardiac pacemaker in claim 3 wherein said pulse width seeking means comprises means for increasing said pulse width to a maximum programmed level during said predetermined timeout period, when capture has not been regained by said amplitude seeking means increasing said pulse width to the maximum programmed level.

* * * * *